United States Patent
Evans et al.

(10) Patent No.: US 11,226,304 B2
(45) Date of Patent: Jan. 18, 2022

(54) APPARATUS AND METHOD FOR ANION DETECTION AND/OR MEASUREMENT

(71) Applicants: University of South Australia, Adelaide (AU); Sentek Pty Ltd, Stepney (AU)

(72) Inventors: Drew Raymond Evans, Mawson Lakes (AU); Sam Rudd, Mawson Lakes (AU); Peter Buss, Woodforde (AU); Michael Reginald Dalton, Greenwith (AU); Michael Robert Portmann, Pasadena (AU)

(73) Assignees: University of South Australia, Adelaide (AU); Sentek Pty Ltd, Stepney (AU)

( * ) Notice: Subject to any disclaimer, the term of this patent is extended or adjusted under 35 U.S.C. 154(b) by 0 days.

(21) Appl. No.: 16/340,442

(22) PCT Filed: Oct. 13, 2017

(86) PCT No.: PCT/AU2017/000218
§ 371 (c)(1),
(2) Date: Apr. 9, 2019

(87) PCT Pub. No.: WO2018/068079
PCT Pub. Date: Apr. 19, 2018

(65) Prior Publication Data
US 2019/0234897 A1    Aug. 1, 2019

(30) Foreign Application Priority Data
Oct. 13, 2016 (AU) ................. 2016904152

(51) Int. Cl.
*G01N 27/22* (2006.01)
*G01N 27/12* (2006.01)
(Continued)

(52) U.S. Cl.
CPC ......... *G01N 27/227* (2013.01); *G01N 27/126* (2013.01); *G01N 27/221* (2013.01); *G01N 33/182* (2013.01); *G01N 33/24* (2013.01)

(58) Field of Classification Search
CPC .. G01N 27/126; G01N 27/221; G01N 27/227; G01N 33/24; G01N 33/182
See application file for complete search history.

(56) References Cited

U.S. PATENT DOCUMENTS

| 4,822,566 A | 4/1989 | Newman |
| 5,403,451 A * | 4/1995 | Riviello ............. G01N 27/3277 204/409 |

(Continued)

FOREIGN PATENT DOCUMENTS

| AU | 2003268594 A1 | 7/2004 |
| WO | 9742494 A1 | 11/1997 |

(Continued)

OTHER PUBLICATIONS

Brooke et al., "Evidence for 'bottom up' growth during vapor phase polymerization of conducting polymers", 2014, Polymer, pp. 3458-3460, vol. 55.

(Continued)

*Primary Examiner* — Clayton E. LaBalle
*Assistant Examiner* — Michael A Harrison
(74) *Attorney, Agent, or Firm* — The Webb Law Firm (57) ABSTRACT

An apparatus for selectively detecting an anion in a medium and/or selectively measuring the concentration of an anion in a medium. The apparatus comprises at least one sensor and a conductive polymer film and is configured such that dielectric and/or electric property changes of the conductive polymer film can be detected by the sensor when the conductive polymer film is in hydraulic contact with the medium or after it has been in hydraulic contact with the (Continued)

medium. Methods of selectively detecting an anion in a medium and/or selectively determining a concentration of an anion in a medium are also provided.

15 Claims, 7 Drawing Sheets

(51) Int. Cl.
*G01N 33/18* (2006.01)
*G01N 33/24* (2006.01)

(56) References Cited

U.S. PATENT DOCUMENTS

| | | | |
|---|---|---|---|
| 5,418,466 A | 5/1995 | Watson et al. | |
| 9,376,533 B2 | 6/2016 | Fabretto et al. | |
| 10,060,873 B2 | 8/2018 | Buss | |
| 2004/0009585 A1* | 1/2004 | Venancio | G01N 27/126 435/287.2 |
| 2008/0150556 A1 | 6/2008 | Han et al. | |
| 2011/0242530 A1 | 10/2011 | Tuli et al. | |
| 2012/0114089 A1 | 5/2012 | Potyrailo et al. | |

FOREIGN PATENT DOCUMENTS

| | | |
|---|---|---|
| WO | 2009015775 A1 | 2/2009 |
| WO | 2013052993 A1 | 4/2013 |
| WO | 2014165910 A1 | 10/2014 |

OTHER PUBLICATIONS

Evans et al., "Structure-directed growth of high conductivity PEDOT from liquid-like oxidant layers during vacuum vapor phase polymerization", 2012, Journal of Materials Chemistry, pp. 14889-14895, vol. 22.

Hutchins et al., "Nitrate-Selective Electrode Developed by Electrochemically Mediated Imprinting/Doping of Polypyrrole", 1995, Analytical Chemistry, pp. 1654-1660, vol. 67, No. 10.

Li et al., "Estimation of Electronegativity Values of Elements in Different Valence States", 2006, The Journal of Physical Chemistry A, pp. 11332-11337, vol. 110.

Stahl, "Routine determination of anions by capillary electrophoresis and ion chromatography", 1994, Journal of Chromatography A, pp. 143-148, vol. 686.

* cited by examiner

APPARATUS AND METHOD FOR ANION DETECTION AND/OR MEASUREMENT

CROSS-REFERENCE TO RELATED APPLICATIONS

This application is the United States national phase of International Application No. PCT/AU2017/000218 filed Oct. 13, 2017, and claims priority to Australian Provisional Patent Application No. 2016904152 filed Oct. 13, 2016, the disclosures of which are hereby incorporated by reference in their entirety.

TECHNICAL FIELD

The present disclosure relates to an apparatus for detecting and/or determining the concentration of certain anions in a medium in which the apparatus is placed and to methods of detecting and/or determining anion concentration of the medium by said apparatus.

BACKGROUND

The measurement of the concentration of anions in media such as water and soil is desirable for agricultural or environmental monitoring purposes. For example, nitrogen ($N_2$) is an essential macronutrient for crop production, mostly taken up by crops in the form of the nitrate ($NO_3^-$) ion. Nitrogen is one of the most expensive nutrients to supply and commercial fertilisers represent the major cost in plant production. Therefore, measuring and monitoring nitrate ion concentration in a medium like soil can help farmers determine nitrogen requirements and avoid the expense and environmental issues associated with over use of fertilisers. Measuring and monitoring nitrate ion concentration can also assist in evaluating plant nutrient uptake mechanisms for specific environmental and agricultural management practices. Furthermore, knowledge of the nutrient profile of a soil prior to application of fertilisers makes it possible to enhance crop yield.

The measurement of the concentration of other anions in media may also be desirable. For example, perchlorate ($ClO_4^-$) is an environmental contaminant that is usually associated with the use of fertiliser. Therefore, monitoring of perchlorate concentration in soil and/or ground water can be used to regulate the use of perchlorate containing fertilisers.

For this purpose, in J. Chromatography, 686: 143-148 (1989), R. Stahl suggests use of ion chromatography to determine levels of anions in soil leachates.

WO 97/42494 discloses a soil nutrient sensing apparatus based on capillary zone electrophoresis (CZE) which requires mixing the soil sample with water to produce a solution and then introducing the solution into a capillary column. This method lacks repeatability at the same spatial position in the soil because it is a destructive sampling technique.

Further sensing apparatus using ion selective electrodes have been developed to detect and measure soil nutrients such as nitrate ion, as described in for example US 2011/0242530 A1 and WO200915775. Specifically, US 2011/0242530 A1 discloses a method of measuring the concentration of an ion in a solution that diffuses or flows into a distal end of a tube through a porous section and a sensing apparatus designed for this method comprises an ion selective electrode. It also discloses the use of transflection dip probes based on Ultraviolet to Visual (UV-VIS) wavelength absorption spectroscopy for measurement of nitrate ion concentration in soil.

However, a disadvantage of sensing apparatus using ion selective electrodes or transflection dip probes is that they are laborious to install because distilled water is initially loaded in a porous element and it then undergoes an equilibration with the surrounding soil solution through diffusion and pressure differential across the porous element. Another problem associated with using this type of sensing apparatus is that there is a significant time delay for each measurement of ion concentration, since ions must diffuse in and out of the pores of the element in order to change the conductance reading.

There is a need for an apparatus for detecting and/or measuring the concentration of anions in a medium that can overcome one or more of the problems associated with the prior art described above. Alternatively, or in addition, there is a need for an apparatus for detecting and/or measuring the concentration of anions in a medium that provides a useful alternative to prior art sensing apparatus.

SUMMARY

The present disclosure arises from the inventors' surprising finding that conductive polymers are able to absorb anions from a solution or other medium without use of an electric field and that optical and electrical properties of the conductive polymer change when anions are absorbed by the polymer. Furthermore, the inventors have found that the amount of change in optical or electrical properties of the conductive polymer film may be proportional to the concentration of anion(s) absorbed into the polymer.

According to a first aspect, there is provided an apparatus for selectively detecting an anion in a medium and/or selectively measuring the concentration of an anion in a medium, the apparatus comprising at least one sensor and a conductive polymer film and configured such that dielectric and/or electric property changes of the conductive polymer film can be detected by the sensor when the conductive polymer film is in hydraulic contact with the medium or after it has been in hydraulic contact with the medium.

In certain embodiments of the first aspect, the sensor is a capacitive based sensor. Therefore, according to a second aspect, there is provided an apparatus for selectively detecting an anion in a medium and/or selectively measuring the concentration of an anion in a medium, the apparatus comprising at least one capacitive sensor and a conductive polymer film and configured such that dielectric and/or electric property changes of the conductive polymer film can be detected by the capacitive sensor when the conductive polymer film is in hydraulic contact with the medium or after it has been in hydraulic contact with the medium.

According to a third aspect, there is provided a method of selectively detecting an anion in a medium, the method comprising contacting the sensor of the first or second aspect with the medium and detecting dielectric and/or electric property changes of the conductive polymer film.

According to a fourth aspect, there is provided a method of selectively determining a concentration of an anion in a medium, the method comprising contacting the sensor of the first or second aspect with the medium, detecting dielectric and/or electric property changes of the conductive polymer film and determining a concentration of the anion from the detected dielectric and/or electric property changes.

According to a fifth aspect, there is provided a use of a conductive polymer film on an apparatus for selectively detecting an anion in a medium and/or selectively measuring the concentration of an anion in a medium, wherein the apparatus is configured such that dielectric and/or electric property changes of the conductive polymer film can be detected by at least one sensor of the apparatus when the conductive polymer film is in contact with the medium or after it has been in hydraulic contact with the medium.

According to a sixth aspect, there is provided a method of preparing an apparatus for selectively detecting an anion in a medium and/or selectively measuring the concentration of an anion in a medium, the method comprising applying a conductive polymer film to a surface of an apparatus comprising at least one sensor.

In certain embodiments of the fifth and sixth aspects, the sensor is a capacitive sensor.

In certain embodiments of the above aspects, the apparatus is configured so that at least part of the conductive polymer film is in hydraulic contact with the medium when the apparatus is positioned in the medium and the conductive polymer film is in electrical communication with the at least one sensor so that dielectric and/or electric property changes of the conductive polymer film can be detected by the at least one sensor.

In certain embodiments of the above aspects, the conductive polymer film is applied onto the apparatus at a position within the sensing electric field of at least one sensor.

In certain embodiments of the above aspects, the sensor is a capacitive sensor having a field of influence and the conductive polymer is positioned in the field of influence. Preferably, the field of influence of the sensor extends to the conductive polymer film but does not extend to the medium to any significant extent. Thus, the field of influence of the sensor is limited to substantially only the conductive polymer film and enclosed circuit and not the abundance of ions or other dielectric contributors in the medium surrounding the sensor. This can be achieved, in some embodiments, by positioning an electromagnetic shield on the apparatus so as to limit the field of influence of the sensor substantially to the conductive polymer. The electromagnetic shield may be a metal film or shield. The electromagnetic shield is configured so that the conductive polymer is in hydraulic contact with the medium when the sensor is positioned in the medium.

In certain embodiments of the above aspects, the conductive polymer is a dopable p-type conducting polymer. Suitable dopable p-type conducting polymer may be selected from the group consisting of, but not limited to, polyaniline, polypyrrole, poly(3-hexylthiophene) (P3HT), poly(3,4-ethylenedioxythiophene) (PEDOT), and a combination thereof.

The present disclosure relates to the specific sensing of one anion only at any one time. The anions to be detected must be mobile to move in and out of the conductive polymer, and must have an affinity for the conductive polymer. The present inventors have shown that nitrate and perchlorate are uptaken preferrentially by PEDOT conductive polymers. On the basis of the electronegativity of the central atom in the anion (nitrogen in the case of nitrate, and chlorine in the case of perchlorate) relative to the electronegativity of the functional atom in the conducting polymer (sulfur in the case of PEDOT) it is possible to extrapolate and expect preferential uptake of sulfate and chloride in PEDOT conductive polymers as well. Electronegativity is defined in, and comparative values taken from, the works of K. Li and D. Xue Journal of Physical Chemistry A 110 (2006) 11332-11337. Thus, in certain embodiments of the above aspects, the anion may be selected from one of nitrate, perchlorate, sulfate, and chloride.

In certain embodiments of the above aspects, the medium may be water, soil, hydroponic growth media (e.g. coco, expanded clay balls, Fytocell, Rockwool, pumice, perlite, vermiculite, etc.), plant tissue, animal tissue, industrial by-products, sludges, a sample or any other suitable aqueous medium. For example, the medium may be an agricultural soil, a body of water such as a river, lake or water catchment, or a sample extracted from or derived from any of these sources. Advantageously, the sensor may be used for in-situ selective detection and/or measurement of the anion. However, it is also contemplated that the sensor be used ex-situ.

In certain embodiments of the above aspects, the conductive polymer film on the apparatus has a thickness of from about 50 nm to about 1000 nm. In certain specific embodiments, the conductive polymer film has a thickness of 150 nm. The conductive polymer film may be formed from a single layer or multiple layers of conductive polymer film may be deposited one atop the other to form a conductive polymer film of desired thickness.

Specific embodiments will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

BRIEF DESCRIPTION OF DRAWINGS

Embodiments will be discussed with reference to the accompanying drawings wherein:

FIG. 7 presents the analysis of reduced PEDOT samples (A to C) that were prepared by electrochemical reduction, and then subsequently exposed to real water samples extracted and supplied from farming land. The water samples were analysed using a standard nitrate "strip test" to determine the concentration of nitrate within, in the parts per million concentration range. Each water sample had one PEDOT film placed within for 1 h, and their electrical conductivity measured before and after soaking. The change in electrical conductivity is recorded as the percentage change in sheet resistance. X-ray Photoelectron Spectroscopy was then conducted on the soaked PEDOT samples to determine the presence of anions, and the atomic concentration of those anions. Only nitrate was present in the PEDOT, despite the real water samples containing a broad spectrum salt species typical of agricultural soil;

DESCRIPTION OF EMBODIMENTS

Figure 1:
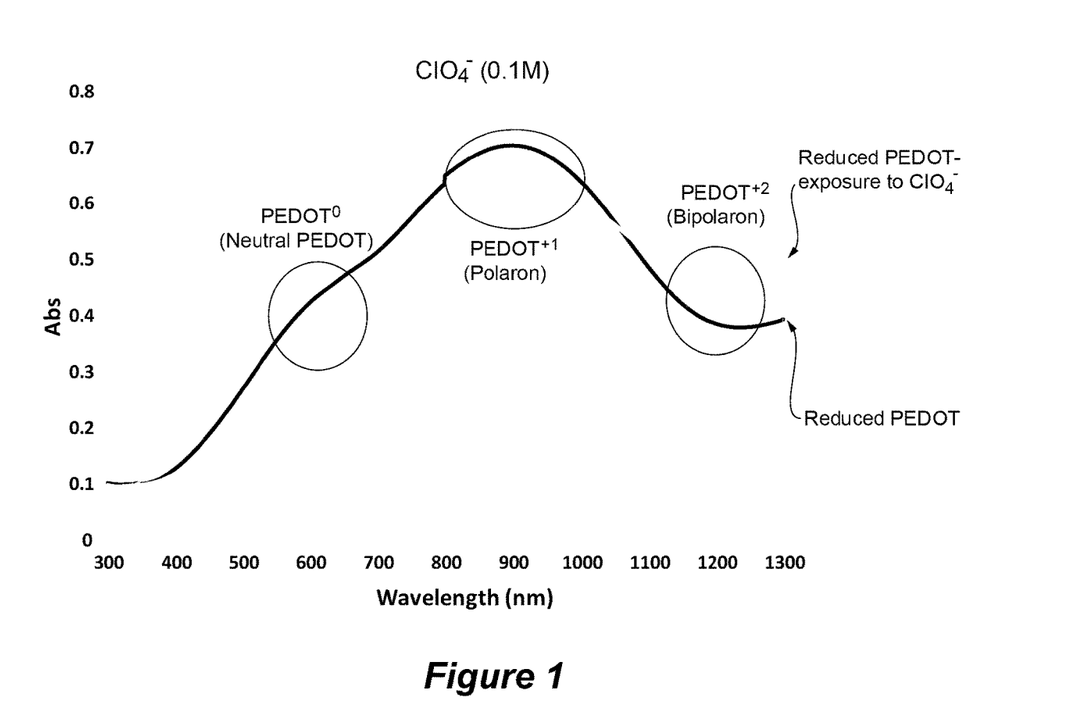
FIG. 1 is a plot of varying optical absorbance over wavelength between 300 nm and 1300 nm for reduced PEDOT and reduced PEDOT after exposure to $ClO_4^-$ (0.1M). The decrease in optical absorption for neutral and polarons, and increase in optical absorption for bipolarons, highlights the increase in doping of the PEDOT as perchlorate anions diffuse into the PEDOT structure. It is well known that changes in optical properties are commensurate with changes in the polymer electrical properties.

As discussed, the present inventors surprisingly found that a conductive polymer changes optical absorption when doped with different levels of anions in the absence of an external electric field, as shown in FIG. 1. Specifically, FIG. 1 is a plot of varying optical absorbance between 300 nm and 1300 nm for reduced PEDOT and reduced PEDOT after exposure to $ClO_4^-$ (0.1M) with no applied electric field. The decrease of neutral and polarons with an increase of bipolarons shows the uptake of $ClO_4^-$ into the PEDOT.

Figure 2:
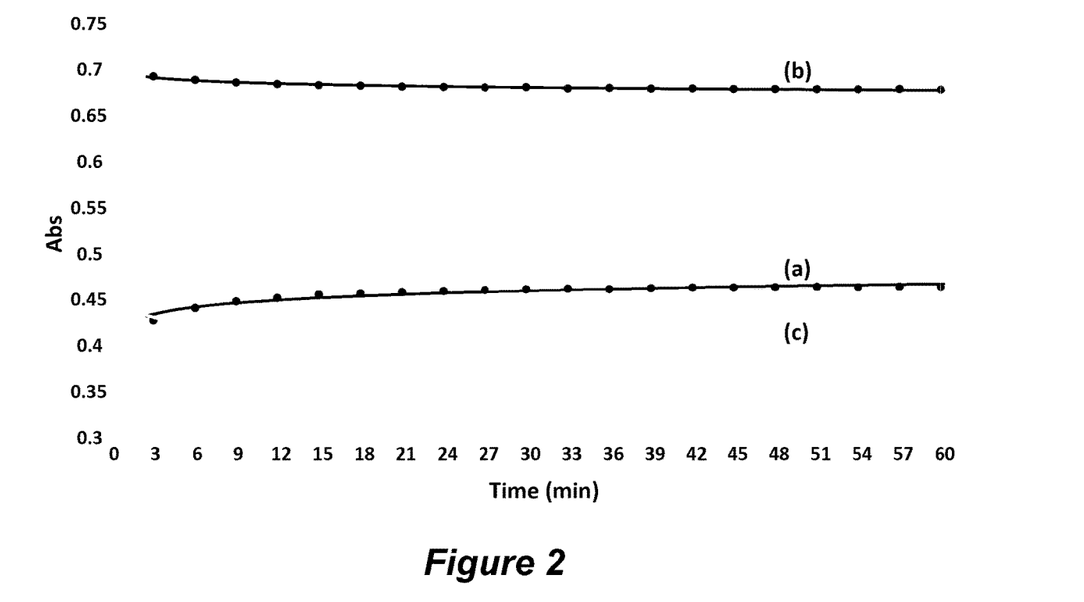
FIG. 2 is a plot of kinetic studies of reduced PEDOT upon exposure to $ClO_4^-$ (0.1M): (a) 1220 nm (Bipolaron)-$ClO_4^-$ (0.1M); (b) 900 nm (Polaron)-$ClO_4^-$ (0.1M); and (a) 600 nm (Neutral)-$ClO_4$ (0.1M). The uptake of $ClO_4^-$ anions occurs over a time frame of less than 1 hour.
Figure 3:
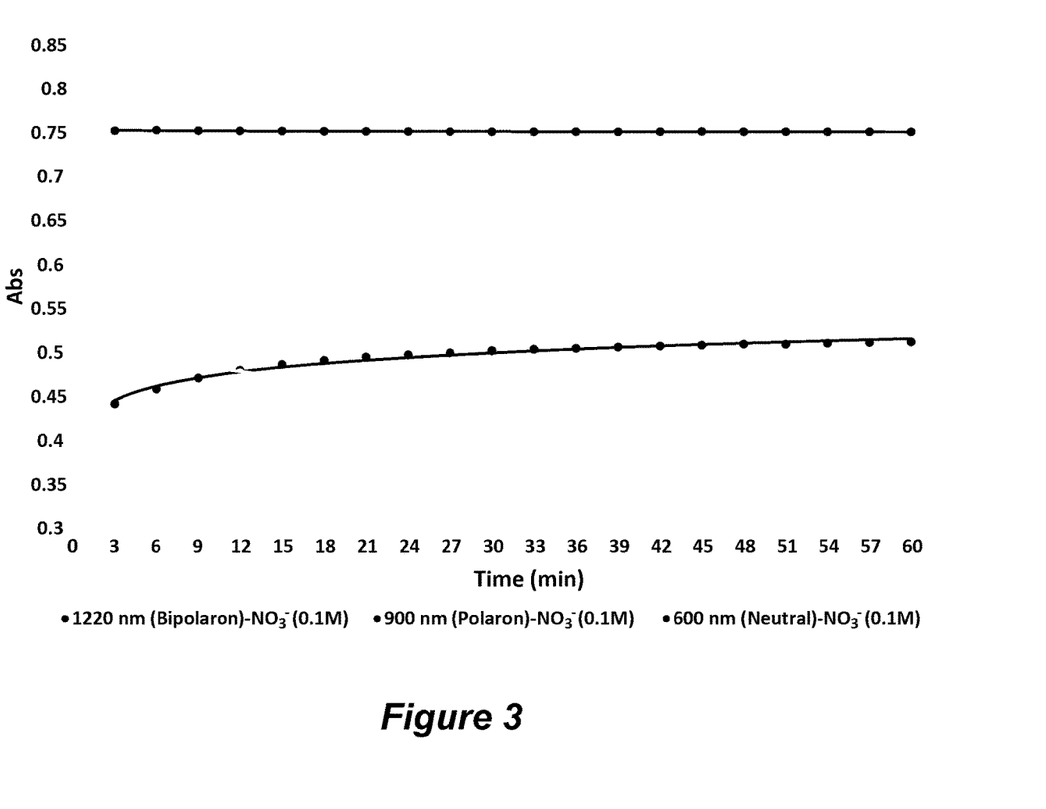
FIG. 3 is a plot of kinetic studies of reduced PEDOT upon exposure to $NO_3^-$ (0.1M). The uptake of $NO_3^-$ anions occurs over a time frame of less than 1 hour. The doping level of the PEDOT is observed to increase given the increase in optical absorption for the bipolarons, and decrease in optical absorption for the neutrals.

As shown in FIG. 2 and FIG. 3, 0.1M perchlorate ($ClO_4^-$) and nitrate ($NO_3^-$) anions dope the conductive polymer over a time period of 1 h. This is measured by the change in optical properties as a function of time in the absence of an external electric field.

Figure 5:
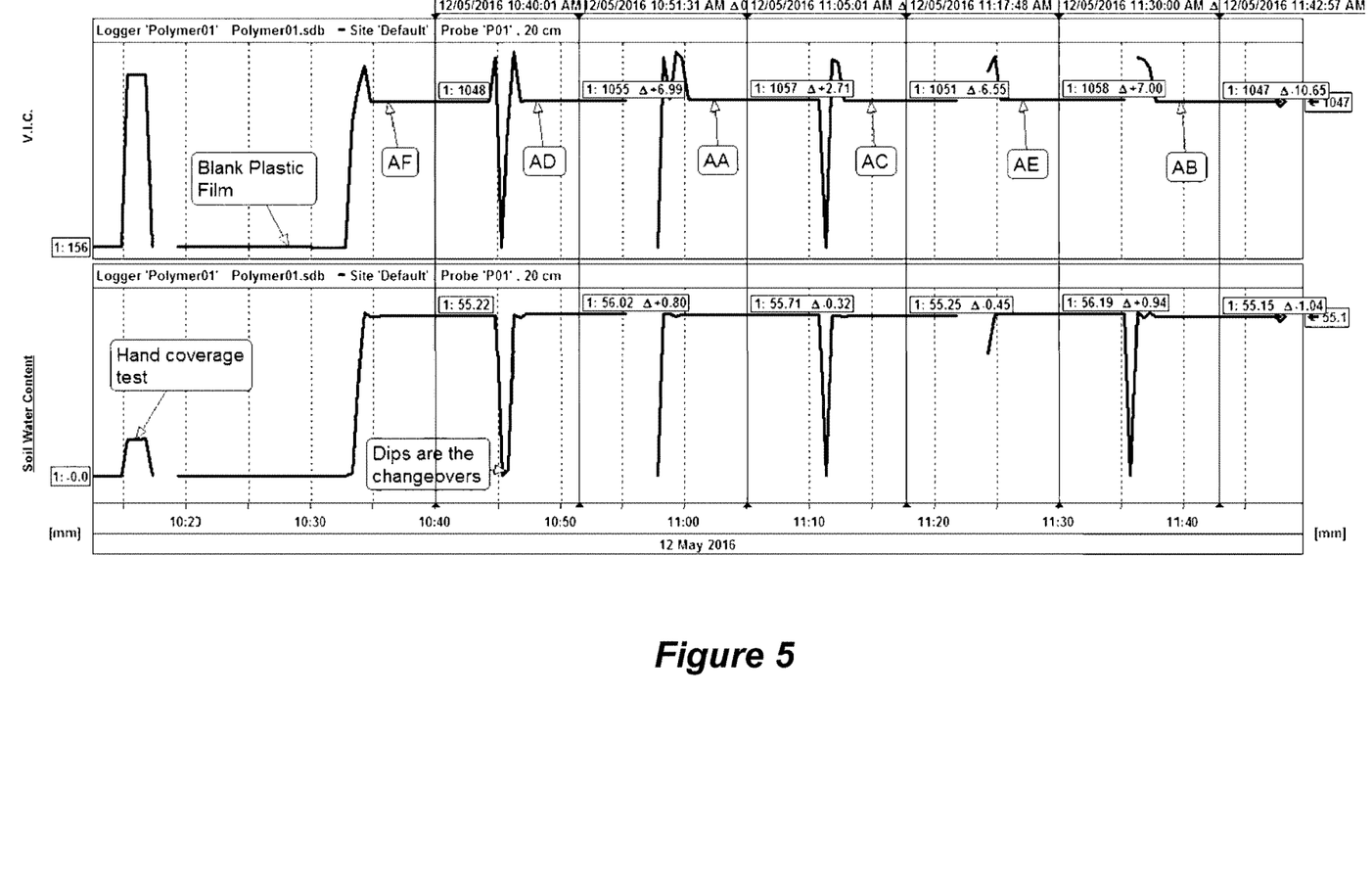
FIG. 5 shows plots of Volumetric Ion Content (VIC, upper pane) and Volumetric Water Content (VWC, lower pane) obtained from reduced metal-shielded PEDOT films (samples 1 through 6) that are obtained by pre-treatment for 2 h by soaking in MilliQ water or electrochemically reduced, and then subsequently exposed to different $NO_3^-$ concentrations for 1 h, tested in triplicate. Higher concentration nitrate-treated PEDOT films are associated with lower VWC and VIC values from the Sentek sensors.
Figure 6:
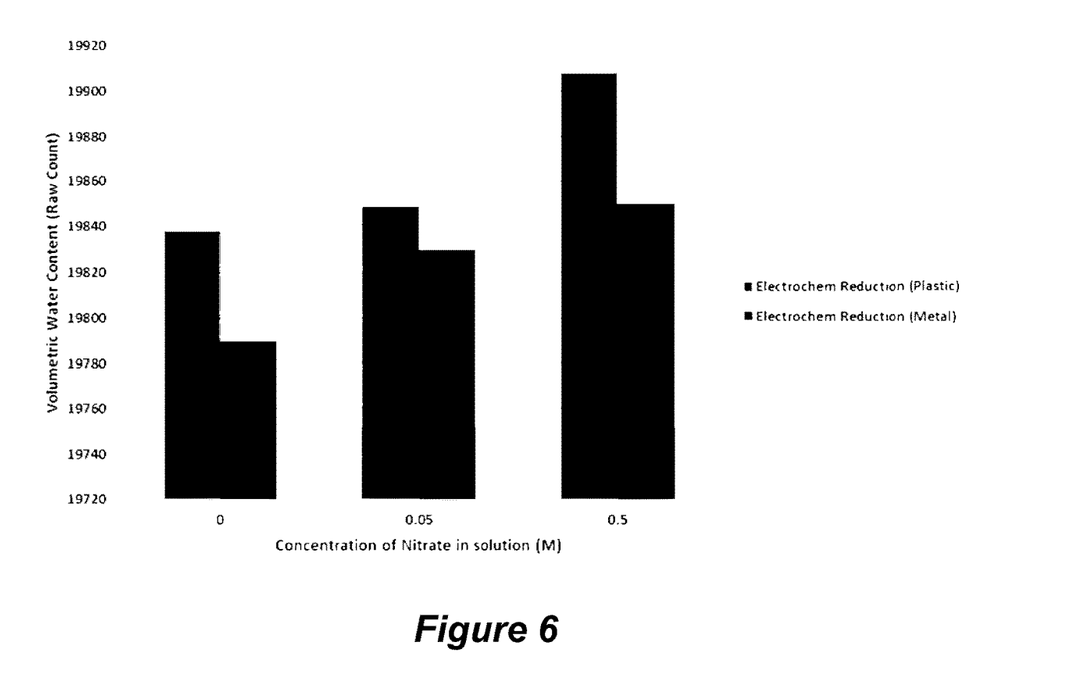
FIG. 6 shows a linear relationship between VWC and VIC raw count values obtained from a single Sentek TriSCAN sensor for 6 different PEDOT films. There is a trend for lower VWC and VIC raw count values to be associated with lower nitrate-treated PEDOT films.

FIG. 5 shows the volumetric ion content (upper pane) and volumetric water content (lower pane) of PEDOT film treatments 1 to 6, wherein 1 to 3 samples were pre-treated by soaking the conductive polymer films in Mill iQ water for 1 h and then soaking in their respective solutions for 1 h, and 4 to 6 samples were pre-treated by electrochemically reducing the conductive polymer films to remove anions from within the conducting polymer and then soaking in their respective solutions for 1 h. It follows that the doping and de-doping of anions can be driven by chemical potential, not just via electric fields. This doping and de-doping can be observed using a capacitive sensor to detect the changing dielectric and/or electric property changes of the polymer. On this basis, a capacitive sensor comprising a conductive polymer film that regulates its doping level in response to changing ion concentration in a medium such as soil or ground water was developed.

Figure 4:
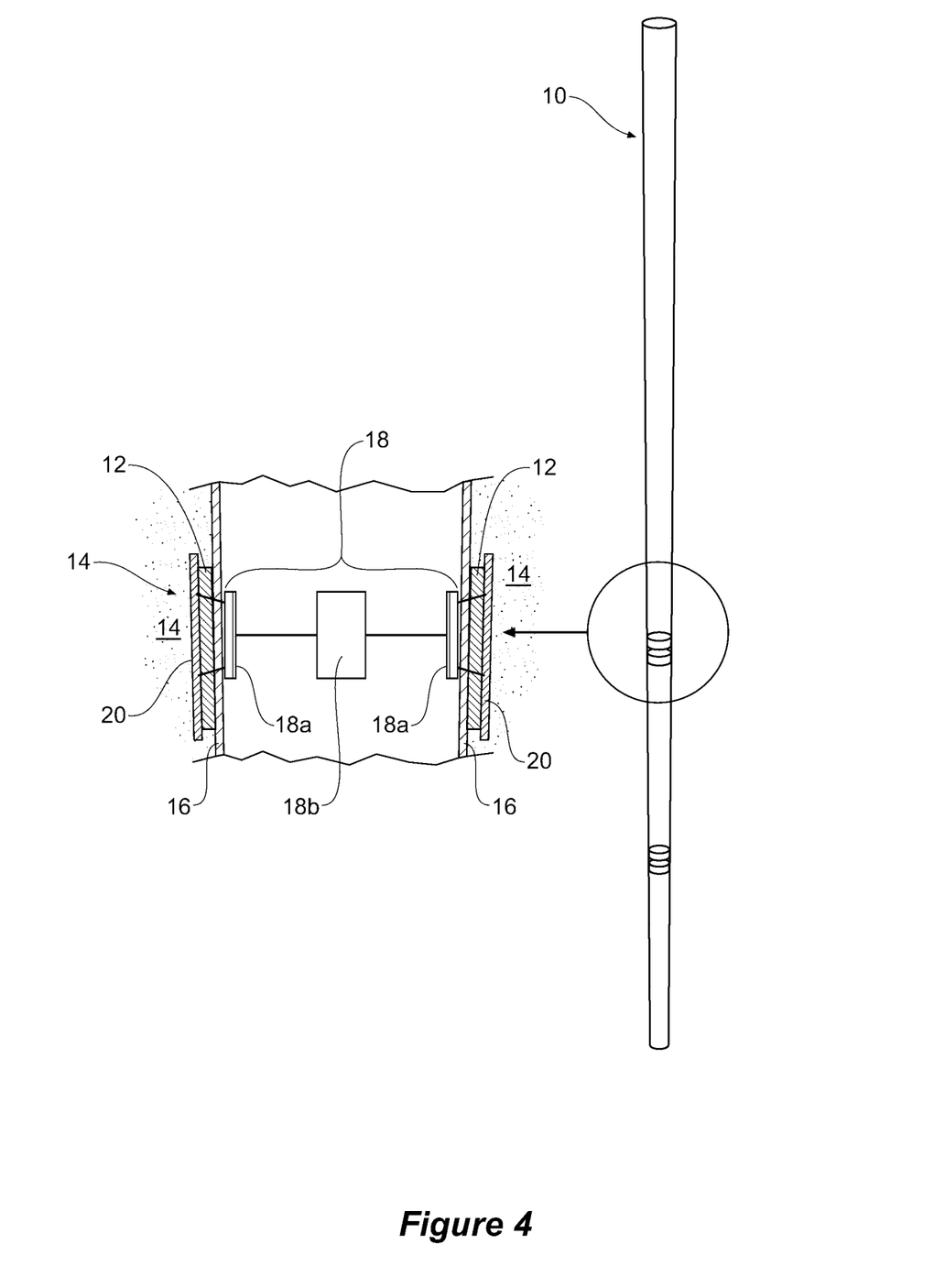
FIG. 4 is an illustrative representation of an embodiment of an apparatus of the present disclosure.

Thus, provided herein is an apparatus 10 for selectively detecting an anion in a medium and/or selectively measuring the concentration of an anion in a medium 14, an illustrative embodiment of which is shown in FIG. 4. The apparatus 10 comprises at least one sensor 18 and a conductive polymer film 12. The sensor 18 is configured such that dielectric and/or electric property changes of the conductive polymer film 12 only can be detected by the sensor 18 when it is in contact or after it has been in hydraulic contact with the medium 14. The sensor 18 is isolated and protected from the polymer 12 and medium 14 by use of a housing 16. In the embodiment illustrated in FIG. 4, the apparatus 10 further comprises an electromagnetic shield 20 (described in more detail later).

In certain embodiments, the sensor 18 is a capacitive sensor. Therefore, also provided herein is an apparatus 10 for selectively detecting an anion in a medium 14 and/or selectively measuring the concentration of an anion in a medium 14. The apparatus 10 comprises at least one capacitive sensor 18 and a conductive polymer film 12. The capacitive sensor 18 is configured such that dielectric and/or electric property changes of the conductive polymer film 12 can be detected by the capacitive sensor 18 when it is in contact or after it has been in hydraulic contact with the medium 14.

The apparatus 10 comprises a housing 16 and the one or more capacitive sensors 18 located internally in the housing. In some embodiments, the apparatus 10 comprises a single capacitive sensor 18. In other embodiments, the apparatus 10 comprises a plurality of capacitive sensors 18. In the latter embodiments, the housing 16 is configured to house the plurality of capacitive sensors 18 along the length of the housing 16. The capacitive sensors 18 are spaced longitudinally apart along a support frame (not shown) at defined distances below the surface of the medium. Each capacitive sensor 18 comprises at least one pair of sensor rings 18a positioned inside the plastic casing 16. The sensor ring(s) 18a form the capacitor of the capacitive sensor 18. The capacitive sensor 18 also comprises a sensor circuit 18b.

Each capacitive sensor(s) 18 can measure the dielectric property of a medium such as soil. Sensors of this type are described in, for example, U.S. Pat. No. 5,418,466 and WO 2014/165910, the details of which are incorporated herein by reference. Other capacitive sensors that may perform the same function could also be used.

Suitable sensor apparatus without the conductive polymer are commercially available from Sentek Pty Ltd (77 Magill Road, Stepney, S.A. 5069, Australia) under the tradenames TriSCAN™, EnviroSCAN™ or Drill & Drop™. These commercially available apparatus are able to measure and distinguish between soil water content and salt content. This information is then processed to calculate soil Volumetric Ion Content (VIC) separately from the Volumetric Water Content. These commercially available apparatus can then be adapted to include the conductive polymer film 12 and electromagnetic shield 20 to provide the apparatus 10.

In use, an electronic circuit is used to transduce changes in the characteristics of the capacitive sensors 18, the signals of which represent changes of the dielectric and/or electric property of the conductive polymer film 12. Signal detection can occur at predetermined time intervals and thus can be used to assess changes over time. In certain embodiments, some of the capacitive sensors 18 can be used to detect changes of the dielectric and/or electric property of the conductive polymer film 12 whilst other capacitive sensors 18 in the same apparatus 10 can be used to measure the moisture and/or the salinity in the surrounding medium 14.

One or more signals representing changes of the dielectric and/or electric property of the conductive polymer film 12 and, optionally, the moisture and/or the salinity in the surrounding medium 14 are then communicated to a data collection device via a cable, a printed circuit or wirelessly from the sensor, as described in WO 2014/165910 A1. In some embodiments, the data is communicated using Bluetooth™ to a mobile device, such as for example a Smart Phone on which an application is available to receive and process data obtained from the apparatus 10.

Power for the apparatus 10 and the data collection device may be provided from any suitable AC or DC power source, such as batteries.

The apparatus 10 may be used as part of a measuring network including sensor circuitry which also reads multiple sensing apparatus which can temporarily store and/or transmit sensor data to an appropriate computer facility, data logger or hand held device.

The apparatus 10 can take any suitable form and may, for example, be in the form of an insertion sensing apparatus, such as a tapered or sharp insertion sensing apparatus for soils or other solid media, a single sensing apparatus for aqueous media or a mesh parallel plate sensing apparatus for use in aqueous solutions. Exemplary forms of apparatus 10 that are different to the form shown in FIG. 4 are shown in FIGS. 8 to 12. In each case, the apparatus 10 comprises two capacitive sensor plates 18 with each capacitive sensor plate 18 coated with a conductive polymer film 12 which is, in turn, shielded by an electromagnetic shield 20 (described in more detail later).

The conductive polymer film 12 is a conductive polymer that (i) is a p-type polymer having the ability to be positively charged, (ii) has the ability to dope and/or de-dope through exchange of anions with its surroundings, and (iii) changes dielectric and/or electric properties after doping or de-doping with anions. Examples of suitable conductive polymers include, but are not limited to, polyaniline, polypyrrole, poly(3-hexylthiophene) (P3HT), poly(3,4-ethylenedioxythiophene) (PEDOT), or combinations thereof. In certain embodiments, the conductive polymer is selected from polypyrrole and poly(3,4-ethylenedioxythiophene) (PEDOT).

In certain embodiments, the conductive polymer film 12 excludes all other ions and dielectric contributors except the specific anion for which the polymer was designed. Thus, it may be possible to select or "tune" the conductive polymer so that it is selective for one anion over one or more other anions. As used herein, the terms "selective", "selectivity" and "selectively" in relation to absorption of one anion into a conductive polymer preferentially over other anions does not necessarily mean the conductive polymer is 100% selective for one specific anion over other anions. It will be appreciated by the skilled person that a relatively low percentage of other anions may also be absorbed but the amount of other anions absorbed is low enough within a required accuracy to not have any measureable effect on measurement of the specific target anion. As such, the terms "selective", "selectivity" and "selectively" may mean that there is a greater than 50%, greater than 60%, greater than 70%, greater than 80%, greater than 90% or greater than 95% preference for one specific anion over other anions. For example, the terms "selective", "selectivity" and "selectively" may mean that there is an 80%, 81%, 82%, 83%, 84%, 85%, 86%, 87%, 88%, 89%, 90%, 91%, 92%, 93%, 94%, 95%, 96%, 97%, 98%, 99% or 100% preference for one specific anion over other anions.

The conductive polymer film 12 may have a thickness of from about 50 nm to about 1000 nm. In some embodiments, a PEDOT film with a thickness of 150 nm is employed. The thickness of the conductive polymer film 12 may be linked to the measurement of specific ions requiring a certain thickness of polymer to attain a certain resolution.

The conductive polymer film 12 with desirable thickness can be prepared by any known method. For example, a PEDOT film can be prepared by vacuum vapour phase polymerisation as described in R. Brooke et al. Polymer 55 (2014) 3458-3460 or in Evans, D., et al. J. Mater. Chem. 22 (2012) 14889-14895. Methods for producing suitable conductive polymer films 12 are described in WO 2013/052993 A1. The conductive polymer film 12 may be formed directly on the housing 16 or it may be formed on a flexible substrate which is then affixed to the housing 16.

The conductive polymer film 12 is positioned on the housing 16 and within an electric field generated by the one or more capacitive sensors 18. In this way, the conductive polymer film 12 is in electrical communication with the sensor 10 so that dielectric and/or electric property changes of the conductive polymer film 12 can be detected by the sensor(s) 18. In other words, the sensor 18 has a field of influence and the conductive polymer film 12 is positioned on the apparatus 10 in the field of influence. Importantly, the field of influence of the sensor 18 extends to the conductive polymer film 12 but does not extend to the medium 14 to any significant extent for those sections of the apparatus 10 that are configured to detect and/or measure anions. In this way, the field of influence of the sensor 18 is limited to only the conductive polymer film 12 and enclosed circuit and not the abundance of ions or other dielectric contributors in the medium 14 surrounding the apparatus 10. This is achieved, in some embodiments, by positioning an electromagnetic shield 20 on the apparatus 10 so as to limit the field of influence of the sensor 18 predominately to the conductive polymer film 12. The electromagnetic shield 20 may be a metal film or a mesh to enable hydraulic contact with the conductive polymer film 12. It will be appreciated that in those embodiments of the apparatus 10 that are used to detect and/or measure one or more anions and also measure the moisture and/or the salinity in the surrounding medium 14, the extent of the field of influence will vary along the length of the apparatus 10 and will be restricted to the conductive polymer film 12 at some vertical positions of the apparatus 10 but will extend to the surrounding medium at other vertical positions of the apparatus 10.

At least part of the conductive polymer film 12 is in hydraulic contact with the medium 14 when the apparatus 10 is positioned in the medium 14. In the illustrated embodiment, the electromagnetic shield 20 covers an outer surface of the conductive polymer film 12.

The electromagnetic shield 20 also helps to protect the conductive polymer film 12 from physical abrasion when the apparatus 10 is inserted into an abrasive medium such as soil. When the electromagnetic shield 20 is present it does not completely cover the conductive polymer film 12 so that the conductive polymer film can remain in hydraulic contact with the medium 14.

In embodiments that are not illustrated, the apparatus 10 may be formed from a plurality of sensor segments. Each sensor segment comprises a capacitive sensor 18. The segments may have connectors that allow for segments to be connected to one another in order to build up a total apparatus 10. Some segments may contain the conductive polymer film 12 and electromagnetic shield 20 and hence be capable of measuring anion concentration in the medium 14 whilst other segments may not contain the conductive polymer film 12 and those segments may be used to measure moisture content or salinity in the medium 14 (e.g. in soil). In these and other embodiments, the apparatus 10 may be used as an ion profiling probe with a multiplicity of sensors 18 arranged vertically throughout the profile and two or more of the sensors 18 capable of selectively measuring different anions and/or different properties of the medium.

The measurable anions may be nitrate ion, perchlorate ion, sulfate ion or chloride ion. Advantageously, the present inventors have found that nitrate and perchlorate ions are selectively absorbed by PEDOT conductive polymer films in the absence of an external electric field to electrochemically drive the anions into or out of the conducting polymer. Thus, the apparatus 10 described herein can be used to selectively detect and/or measure the concentration of nitrate or perchlorate ions in a medium.

The apparatus 10 can be used in a method of selectively detecting an anion in a medium. The method comprises hydraulically contacting the apparatus 10 with a medium 14 and detecting dielectric and/or electric property changes of the shielded conductive polymer film 12.

The apparatus 10 can also be used in a method of selectively determining a concentration of an anion in a medium. The method comprises hydraulically contacting the apparatus 10 with a medium 14, detecting dielectric and/or electric property changes of the conductive polymer film 12 and determining a concentration of the anion from the detected dielectric and/or electric property changes. In one embodiment the output of the apparatus 10 is calibrated for the anion concentration against standard or analytical test methods such as standard strip tests or ion chromatography or inductively coupled plasma mass spectrometry using reference liquids of known target anion concentration before deployment in the field.

Also provided herein is a use of a conductive polymer film 12 on an apparatus 10 for selectively detecting an anion in a medium 14 and/or selectively measuring the concentration of an anion in a medium 14. The apparatus 10 is configured such that dielectric and/or electric property changes of the conductive polymer film 12 can be detected by the apparatus 10 when it is in contact with the medium 14.

Also provided herein is a method of preparing an apparatus 10 for selectively detecting an anion in a medium 14 and/or selectively measuring the concentration of an anion in a medium 14. The method comprises applying a conductive polymer film 12 to a surface of an apparatus 10. If desired, the apparatus 10 can be equipped with other sensors for measurement, such as temperature, soil water, soil salinity, and other specific anion(s) sensors, so that measurements for different properties of a medium are achievable at the same time.

EXAMPLES

Embodiments of the present disclosure are further described in the following non-limiting examples.

PEDOT films were synthesised based on the methods described in WO 2013/052993 A1 on cleaned substrates, such as microscope glass slide, flexible plastic and aluminium foil, using the vapour phase polymerisation (VPP process). Prior to polymerisation, the oxidant solution, containing Fe(III) Tosylate, ethanol, butanol and block copolymers poly(ethylene glycol-propylene glycol-ethylene glycol) (PEG-PPG-PEG) of Mw=5800, was directly spin-coated (400B-6NPP, Laurell Technologies Inc.) onto substrate at 1500 rpm for 25 s and then placed on a hotplate set to 70° C. for 30 s to evaporate the solvents. Samples were then removed from the hotplate and placed into a polymerisation chamber (Binder Vacuum Oven-VD 115) set to 35° C.

After polymerisation, PEDOT films were carefully washed by ethanol to remove any unreacted species and existing oxidant solution. Since PEDOT is almost fully doped via the VPP process, a three electrode system in an electrochemical cell was employed to electrochemically reduce the PEDOT films in the presence of a standard Ag/AgCl electrode (3.8M KCl) as the reference electrode in order to remove most of the anions from the PEDOT films. This renders the PEDOT lower in conductivity, and higher in opacity, due to the lower number of anions within the polymer. The reduced PEDOT films were then exposed to prepared salt solutions with different concentrations or extracted water samples from the field provided by Sentek Pty Ltd.

The sheet resistance (Rs) was measured using a Jandel four point probe, and the surface chemistry of the polymer films was analysed using a SPECS (SAGE, Phoibos 150-HSA) X-ray photoelectron spectroscopy (XPS) system fitted with a non-monochromated aluminium anode, with a power of 200 W and a base pressure of $2 \times 10^{-6}$ Pa. Curve fitting was performed with Casa XPS (Neil Fairley, U.K.), using a linear background. Spectra were charge corrected relative to the aliphatic carbon peak at 285 eV. A Cary 5000 UV-Vis NIR spectrophotometer (Agilent Technologies, CA, USA) was used in order to investigate the optical properties of the PEDOT when in contact with different anions.

Figure 7:
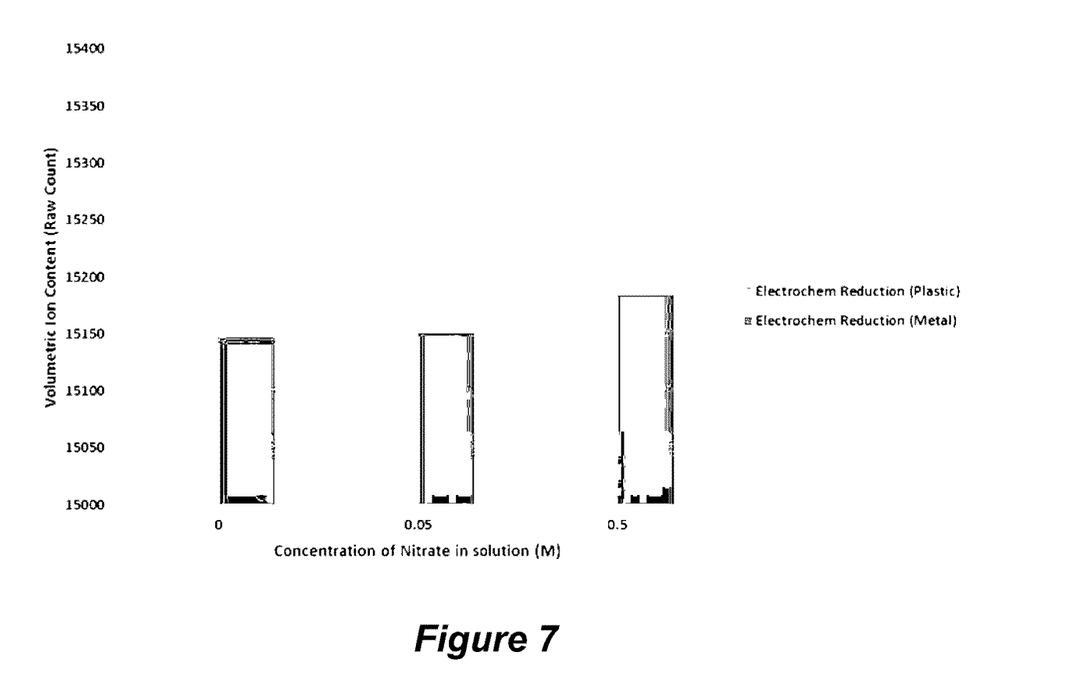
Figure 8:
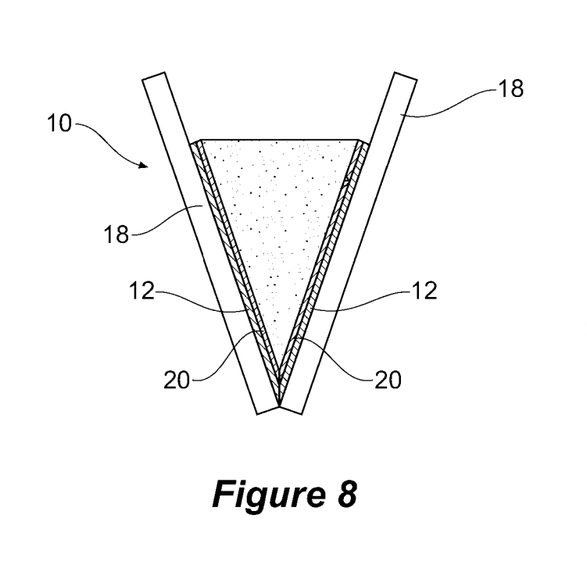
FIG. 8 is an illustrative representation of an alternative embodiment of a capacitive based sensor of the present disclosure.
Figure 9:
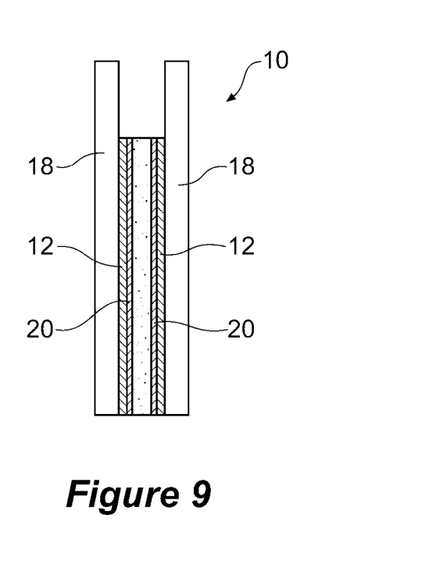
FIG. 9 is an illustrative representation of an alternative embodiment of an apparatus of the present disclosure.
Figure 10:
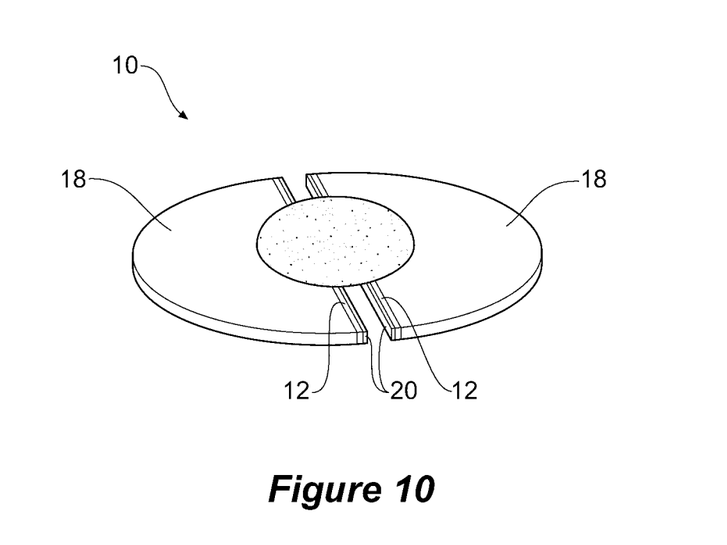
FIG. 10 is an illustrative representation of an alternative embodiment of an apparatus of the present disclosure.
Figure 11:
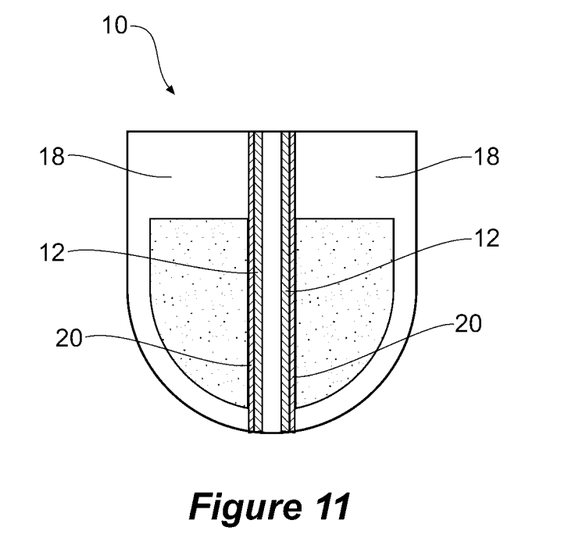
FIG. 11 is an illustrative representation of an alternative embodiment an apparatus of the present disclosure.
Figure 12:
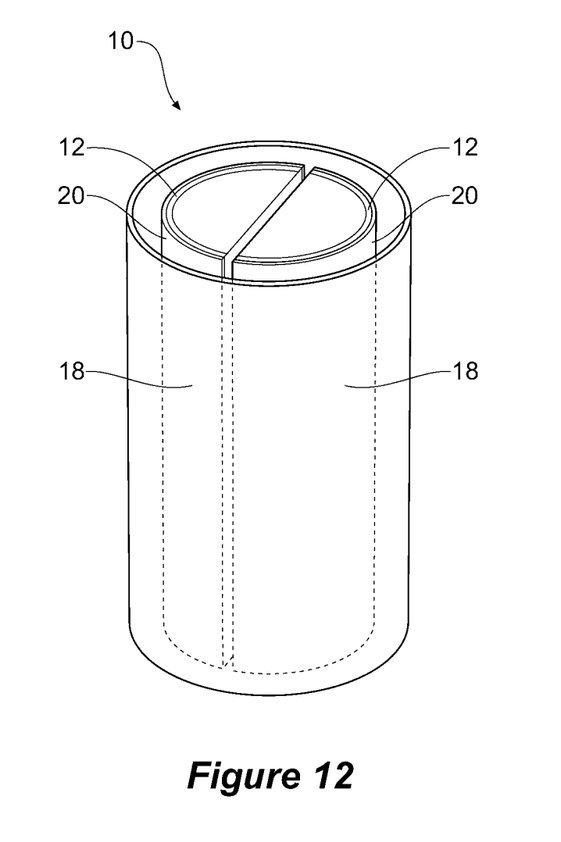
FIG. 12 is an illustrative representation of an alternative embodiment of an apparatus of the present disclosure.

FIG. 7 contains information for PEDOT films that were prepared on plastic and metal substrates. These substrates were thin enough to make them flexible. These flexible PEDOT films were exposed to control salt solutions of different nitrate concentrations in MilliQ water for 1 h. The samples were then air dried and wrapped around the plastic housing that encases the TriSCAN sensor. Raw count values from the sensor were recorded that in normal operation of the sensor would convert to a Volumetric Water Content (VWC) and Volumetric Ion Content (VIC). For both substrates a trend was observed between the amount of nitrate in the PEDOT and the output of the TriSCAN sensor. Introducing the metal substrate to the outside of the PEDOT to confine the TriSCAN sensor's field of influence to be within the PEDOT only yields the same trend.

Table 1 shows data for an example where reduced PEDOT was exposed to real water samples taken from agricultural soil. The PEDOT was prepared via vacuum vapour phase polymerisation, and subsequently reduced via electrochemical means. Upon exposure to the three different water samples, the PEDOT films A to C had a change in electrical properties as measured by the change in sheet resistance between before and after exposure to the water samples. The magnitude of the electrical change correlates with the amount of nitrate determined in the water samples using the standard "strip test". Importantly the uptake of nitrate only in the PEDOT films was confirmed using X-ray Photoelectron Spectroscopy. The atomic percentage of nitrogen in each PEDOT film correlated with both the "strip test" and the change in electrical properties. This example further demonstrates the sensitivity of PEDOT films to nitrate concentrations relevant for agricultural use, in the parts per million range.

TABLE 1

| Sample | Concentration of Nitrate (ppm) | Change in Sheet Resistance (%) | Atomic % of N |
|---|---|---|---|
| 1 | 0 | 25.9 | 0.45 |
| 2 | 10 | 28.2 | 0.67 |
| 3 | 100 | 31.4 | 0.75 |

Throughout the specification and the claims that follow, unless the context requires otherwise, the words "comprise"

and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications, and substitutions without departing from the scope of the invention as set forth and defined by the following claims.

The invention claimed is:

1. An apparatus for selectively detecting an anion in a medium and/or selectively measuring the concentration of an anion in a medium, the apparatus comprising at least one capacitive sensor and a conductive polymer film and configured such that dielectric and/or electric property changes of the conductive polymer film can be detected by the capacitive sensor in the absence of an external electric field when the conductive polymer film is in hydraulic contact with the medium to dope or de-dope the conductive polymer film with anions or after it has been in hydraulic contact with the medium to dope or de-dope the conductive polymer film with anions.

2. The apparatus according to claim 1, wherein the conductive polymer film is positioned within a sensing electric field of at least one capacitive sensor of the apparatus.

3. The apparatus according to claim 1, wherein the capacitive sensor(s) has a field of influence and the conductive polymer is positioned in the field of influence of at least one capacitive sensor of the apparatus.

4. The apparatus according to claim 3, wherein the field of influence of the capacitive sensor is restricted substantially to the volume of the conductive polymer film.

5. The apparatus according to claim 4, wherein the field of influence of the capacitive sensor is restricted to the volume of the conductive polymer film by an electromagnetic shield on the conductive polymer film.

6. The apparatus according to claim 5, wherein the electromagnetic shield on the conductive polymer film is a metallic shield.

7. The apparatus according to claim 1, wherein the apparatus is configured so that at least part of the conductive polymer film is in hydraulic contact with the medium when the apparatus is positioned in the medium and the conductive polymer film is in electrical communication with at least one capacitive sensor so that dielectric and/or electric property changes of the conductive polymer film can be detected by the at least one capacitive sensor.

8. The apparatus according to claim 1, wherein the conductive polymer is a dopable or de-dopable p-type conducting polymer.

9. The apparatus according to claim 8, wherein the conductive polymer is selected from the group consisting of: polyaniline, polypyrrole, poly(3-hexylthiophene) (P3HT), poly(3,4-ethylenedioxythiophene) (PEDOT), and a combination thereof.

10. The apparatus according to claim 1, wherein the anion is selected from nitrate, perchlorate, sulfate or chloride.

11. The apparatus according to claim 1, wherein the medium is water.

12. The apparatus according to claim 1, wherein the medium is soil.

13. The apparatus according to claim 1, wherein the medium is selected from hydroponic growth media, coco, expanded clay balls, Fytocell, Rockwool, pumice, perlite, vermiculite, plant tissue, animal tissue, industrial by-products, sludges, and a sample.

14. A method of selectively detecting an anion in a medium, the method comprising contacting the apparatus of claim 1 with the medium and detecting dielectric and/or electric property changes of the conductive polymer film.

15. A method of selectively determining a concentration of an anion in a medium, the method comprising contacting the apparatus of claim 1 with a medium, detecting dielectric and/or electric property changes of the conductive polymer film and determining a concentration of the anion from the detected dielectric and/or electric property changes.

* * * * *